United States Patent [19]

Brooks

[11] 4,247,774
[45] Jan. 27, 1981

[54] SIMULTANEOUS DUAL-ENERGY COMPUTER ASSISTED TOMOGRAPHY

[75] Inventor: Rodney A. Brooks, Bethesda, Md.

[73] Assignee: The United States of America as represented by the Department of Health, Education and Welfare, Washington, D.C.

[21] Appl. No.: 918,804

[22] Filed: Jun. 26, 1978

[51] Int. Cl.² .............................................. G01T 1/20
[52] U.S. Cl. ................................. 250/367; 250/445 T
[58] Field of Search ................... 250/445 T, 367, 363, 250/362, 361

[56] References Cited

U.S. PATENT DOCUMENTS

| | | | |
|---|---|---|---|
| 3,399,302 | 8/1968 | Carrell | 250/367 |
| 4,029,963 | 6/1977 | Alvarez | 250/445 T |

Primary Examiner—Craig E. Church
Attorney, Agent, or Firm—Browdy and Neimark

[57] ABSTRACT

A dual-energy detector system for use in computer assisted tomography. This system produces two independent sets of information from one scan, namely, high-energy and low-energy data. The system employs two cooperating detectors. The first one responds primarily to low-energy photons, allowing most high-energy photons to pass through. The second detector lies behind the first and detects the remaining photons. Thus, two electrical signals are generated which contain information in two different energy ranges, which signals can be computer-processed. The attenuation coefficients at these two energies are sufficiently different so that differential diagnosis and chemical identification may be aided. The computer-processed signals may be employed to provide any of (a) beam-hardening correction, (b) chemical identification and composition of tissues, such as lesions, bone, etc., (c) localization of injected contrast material, or (d) attenuation coefficients for radiation therapy planning.

13 Claims, 5 Drawing Figures

SIMULTANEOUS DUAL-ENERGY COMPUTER ASSISTED TOMOGRAPHY

FIELD OF THE INVENTION

This invention relates to computer assisted tomography systems, and more particularly to computer assisted tomography systems of the dual-energy type.

BACKGROUND OF THE INVENTION

Several recent investigations of dual-energy computed tomography (References 1 to 5) involve changing the X-ray tube voltages for respective scans, for example, from 100 kVp to 140 kVp (kVp=kilovolts peak). Because of differences in chemical composition and effective atomic number of the scanned tissues, the energy dependence of the computed tomography number will be different for various tissues. Thus, high Z elements like calcium and iodine may be identified, and types of soft tissues and tumors may be differentiated.

The previously developed dual-kVp system requires two separate scans for each slice, causing a problem of registration, since the patient may move between the scans. Since two scans are required, the procedure is relatively time-consuming. Also, energy discrimination is somewhat unsatisfactory.

As a result of a preliminary search, the following prior U.S. patents appear to be of interest:
Hounsfield, U.S. Pat. No. 4,052,619
Barbier, U.S. Pat. No. 4,053,779
Allemand, U.S. Pat. No. 4,055,767
Pasedach, U.S. Pat. No. 4,064,393
Ruhrnschopf et at, U.S. Pat. No. 4,065,397
Frogatt, U.S. Pat. No. 3,996,467.

The background of the present invention is further disclosed by the following reference publication:

1. R. A. Rutherford, B. R. Pullan, I. Isherwood, "Measurement of Effective Atomic Number and Electron Density Using an EMI Scanner", 11:15-21, Neuroradiol., Jan. 1976.

2. M. J. Derggren, G. T. Herman, P. Ruefsegger, et al, "Computer Assisted Tomography of Small Quantities of Selected Materials" (Abstract), J. Comput.Assisted Tomog., 1:254-255, Apr. 1977.

3. L. M. Zatz, "The Effect of the kVp Level on EMI Values, Selective Imaging of Various Materials with Different kVp Settings", Radiology, 119:683-688, June 1976.

4. R. E. Latchaw, J. T. Payne, L. H. A. Gold, "Effective Atomic Number and Electron Density as Meaured with a CT Scanner: Computation and Correlation with Brain Tumor Histology". Presented at the 15th Annual Meeting of the American Society of Neuroradiology, Bermuda, Mar. 27-31, 1977.

5. L. Dubal, U. Wiggli, "Tomochemistry of the Brain", J. Comput. Assisted Tomog., 3:300-307, July 1977.

6. R. E. Alvarez, A. Macoviski, "Energy-selective Reconstructions in X-ray Computerized Tomograph.", Phys. Med. Biol. 21:733-744, Sept. 1976.

7. E. C. McCullough, H. L. Baker, O. W. Houser, et al, "An Evaluation of the Quantitative and Radiation Features of a Scanning X-ray Transverse Axial Tomograph: the EMI Scanner", Radiology, 111:709-715, June 1974.

SUMMARY OF THE INVENTION

The present invention aims to accomplish the same purpose as the previously developed dual-kVp system by the use of a split-detector array. The advantage of the split-detector system is that only one scan is required, with consequent elimination of the image registration problem. The system also provides somewhat better energy separation than the previous method using 100 kVp and 140 kVp.

Other possible applications are the elimination of the need for a "precontrast" scan before injecting iodinated contrast material, and the prediction of attenuation coefficients in radiation therapy. Finally, and possibly most importantly, the system may be used to implement a suggestion of Alvarez and Macoviski (6) for correcting the raw data in order to eliminate beam-hardening artifacts.

The split-detector technique* requires two detectors back-to-back in the path of the X-ray beam. The first detector captures mostly low-energy photons while the second detector captures the remaining high-energy photons. The method may be implemented using scintillation, gas ionization, or other types of detectors.

*See (A) Brooks et al, "Split-Detector Computed Tomography: A Preliminary Report", Radiology, Vol. 126, No. 1, pp. 255-257 (Jan. 1978); and (B) R. A. Brooks, "A Quantitative Theory of the Hounsfield Unit and its Application to Dual-Energy Scanning", J. Comput. Assist. Tomog., 1 (4):487-493, Oct. 1977; both (A) and (B) are hereby incorporated by reference.

Accordingly, objects of the invention are to provide for improved tomography; to overcome deficiencies in the prior art, such as those noted above, e.g. to provide an improved dual-energy computer assisted tomography system which overcomes the deficiencies and disadvantages of the previously known dual-energy techniques.

A further object of the invention is to provide an improved dual-energy computer assisted tomography system which can obtain dual-energy slice data using only one scan, thereby avoiding registration problems arising with two scans.

A still further object of the invention is to provide an improved dual-energy computer assisted tomography system which can obtain dual energy slice data with a minimum expenditure of time and with improved energy discrimination.

A still further object of the invention is to provide an improved dual-energy computer assisted tomography system which employs a split-detector array, enabling thedual-energy slice data to be obtained in a single scan.

A still further object of the invention is to provide an improved split-detector arrangement for obtaining simultaneous dual-energy slice data in a single scan in a computer assisted tomography system, employing a detector system such as back-to-back crystals through which the X-ray beam passes sequentially, and wherein the first detector responds primarily to the low-energy photons and the second detector responds to the remaining (high-energy)photons, enabling respective low and high energy sets of slice data to be obtained simultaneously.

A still further object of the invention is to provide an improved dual-energy computer assisted tomography system which can simultaneously obtain dual energy slice data in a single scan and wherein the signals obtained may be employed to provide beam-hardening corrections, chemical identification of lesions, or localization of injected contrast material.

A still further object of the invention is to provide an improved dual-energy computer assisted tomography system wherein differential diagnosis and chemical identification is aided by employing a split-detector energy-discrimminaing array, enabling dual-energy slice data to be obtained in a single scan and utilization the difference in attenuation coefficients for the different energy levels separated out by said split-detector array.

BRIEF DESCRIPTION OF THE DRAWINGS

Further objects and advantages of the invention will become apparent from the following description of an exemplary embodiment and from the accompanying drawings, wherein.

DESCRIPTION OF A PREFERRED EMBODIMENT

Figure 1:
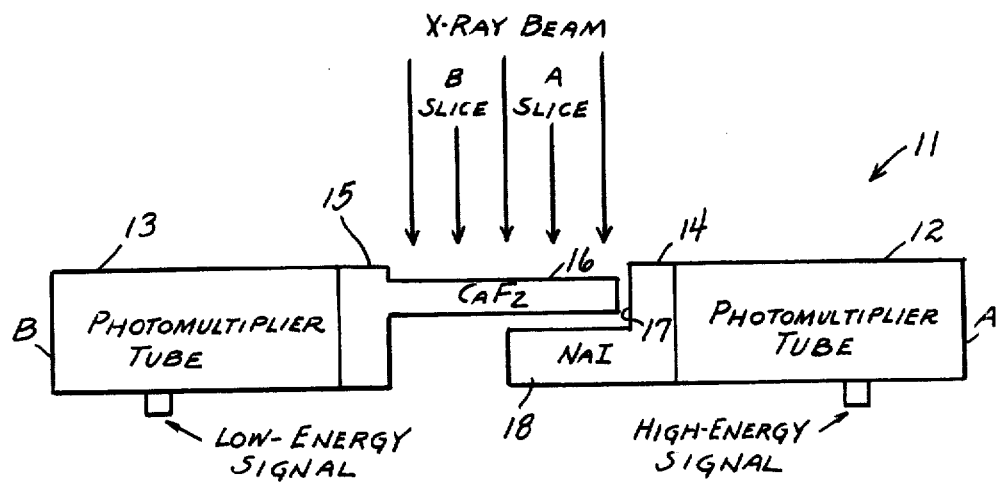
FIG. 1 is a schematic diagram of a split-detector system for computer assisted tomography according to the present invention.

Referring to the drawings, a split-detector system according to the present invention is schematically illustrated in FIG. 1 and is designated generally at 11. The system 11 comprises respective detector units A and B, including the photomultiplier tubes 12 and 3 provided with responsive scintillation crystals 14 and 15. This embodiment was designed to fit into and be compatible with an EMI Mark I X-rayscanner.

The crystal 15 is formed with a relatively thin portion 16 which is received in a rectangular recess 17 formed in crystal 14 and overlies a relatively thick resultant lower portion 18 of crystal 14. As shown, an "A-slice" portion of the X-ray beam passes through the crystal portions 16 and 18 sequentially. The functions of the first crystal detector portion 16 is to respond primarily to the low-energy photons. This requires that the crystal have a strong photoelectric absorption and also that it be fairly thin, Sodium iodide (NaI) is not preferred, because its absorption coefficient is relatively high and its mechanical properties are poor, so that it would be too brittle at the required small thickness unless suitably supported by a very low absorption material. Calcium fluoride ($CaF_2$), on the other hand, is a sturdier material with a moderately strong photoelectric absorption, and therefore is a preferable material for the intended purpose. Various thicknesses of $CaF_2$ crystal detector elements may be employed. For example, $CaF_2$ crystal elements of thicknesses 4, 6 and 8 mm were fabricated to fit directly into the detector housing of an EMI computer assisted tomography apparatus.

The function of the second crystal detector element 18 is to capture the remaining photons. In this case, thinness is not a requirement, and therefore NaI is a satisfactory choice. As above mentioned, the front portion of the NaI crystal is removed at recess 17 to make room for the $CaF_2$ detector element 16, and the remainder is reclad with aluminum, or other suitable material.

Figure 2:
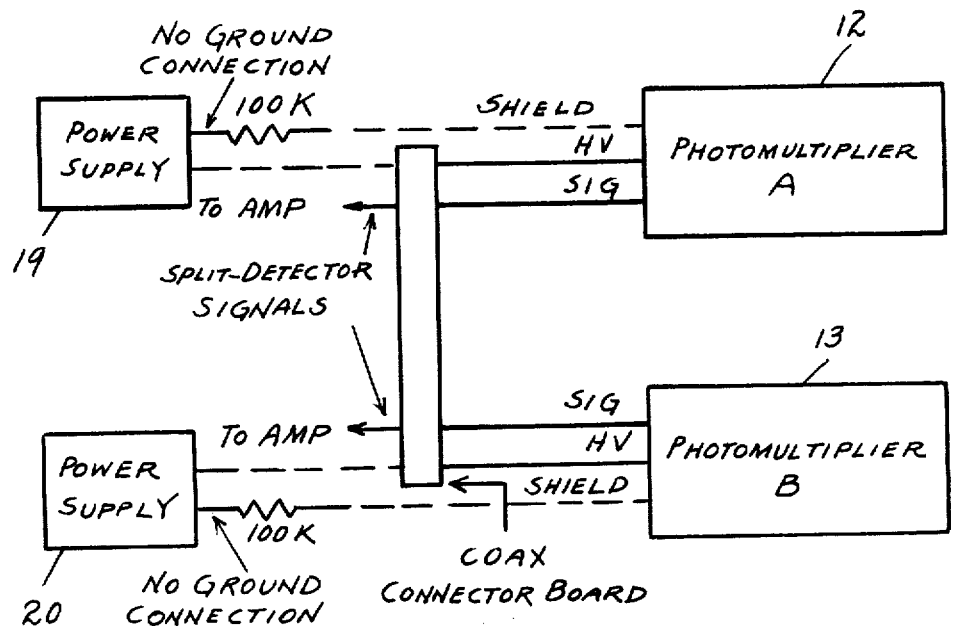
FIG. 2 is a connection diagram for the high voltage power supplies associated with the photomultiplier tubes of the detectors, indicating by dashed lines new coaxial cables that temporarily replace existing cabling in a conventional EMI computer assisted tomography apparatus.

In order to have independent control over the gains of the respective detectors, the photomultiplier tubes are preferably powered by separate power supplies 19 and 20, as shown in FIG. 2, such as Fluke 412B high voltage supplies. Complete changeover of the above-mentioned EMI Mark I apparatus for phantom scans involves replacing the two crystals and changing the high-voltage cables. No alignment adjustments are needed.

Figure 3:
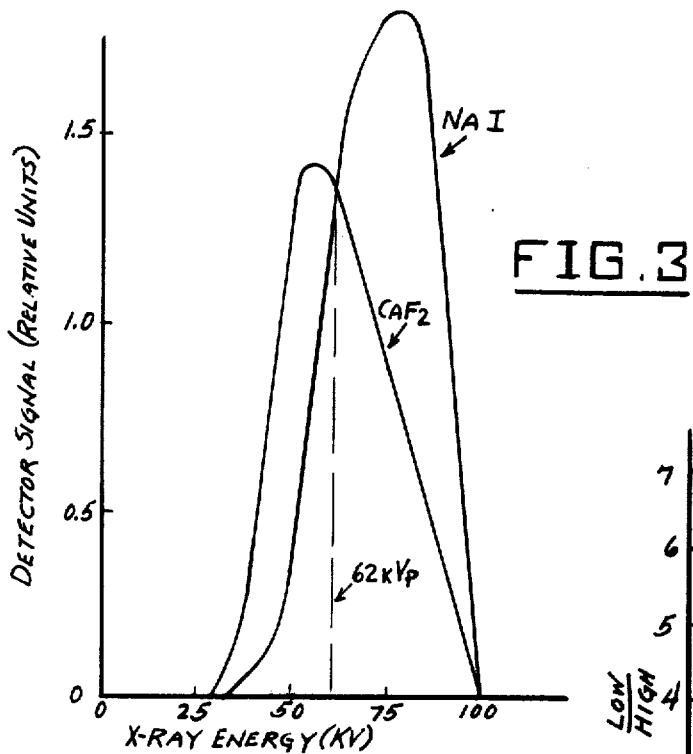
FIG. 3 is a graph showing the detector signals as functions of X-ray energy for the split-detector systems, assuming a 6 mm thick $CaF_2$ crystal for the front detector, a very thick NaI crystal for the back detector, and an operating voltage of 100 kVp.

For providing a better understanding of the operation of the detector system, calculation of spectral response will be described in connection with a typical application. Thus, the emergent X-ray spectrum was calculated, assuming a continuous 100 kVp bremsstrahlung spectrum at the anode, followed by 4.5 mm aluminum and 27 cm water filtration. These figures are typical for an EMI Mark I scanner (see Reference 7). FIG. 3 shows the relative response of the two detectors, assuming the use of a 6 mm thick $CaF_2$ crystal element 16. Only photoelectric absorption was considered in the $CaF_2$ crystal, and the NaI crystal was assumed to capture all the remaining energy. it is to be noted from FIG. 3 that the two detectors have equal response for 62 keV photons, while the $CaF_2$ detector dominates at lower energies and the NaI detector at high energies. As a comparison, FIG. 4 shows the exit spectra for the prior art, two-scan, dual-kVp method.

Figure 5:
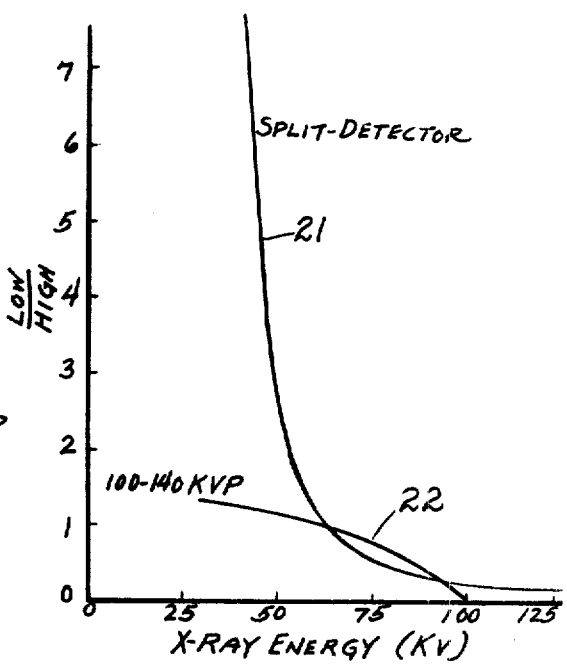
FIG. 5 is a graph showing the ratio of low and high energy signals for the two situations shown in FIGS. 3 and 4.

The energy discrimination is illustrated in FIG. 5, which is a plot of the ratio of the $CaF_2$ and NaI signals as a function of photon energy. This plot does not depend on beam spectrum or absorber thickness, but merely on detector dimensions. The plot for a split-detector system, as described herein, is shown at 21, whereas the plot for a prior art, two-scan, dual-energy system is shown at 22, namely, the plot of the ratio of the dual-energy signals when the voltage is changed from 100 kVp to 140 kVp. This curve 22 is merely the ratio of the numbers of photons produced of a given energy at the two kVp settings, assuming that the tube currents are adjusted so that the numbers of photons at 62 keV are equal.

Figure 4:
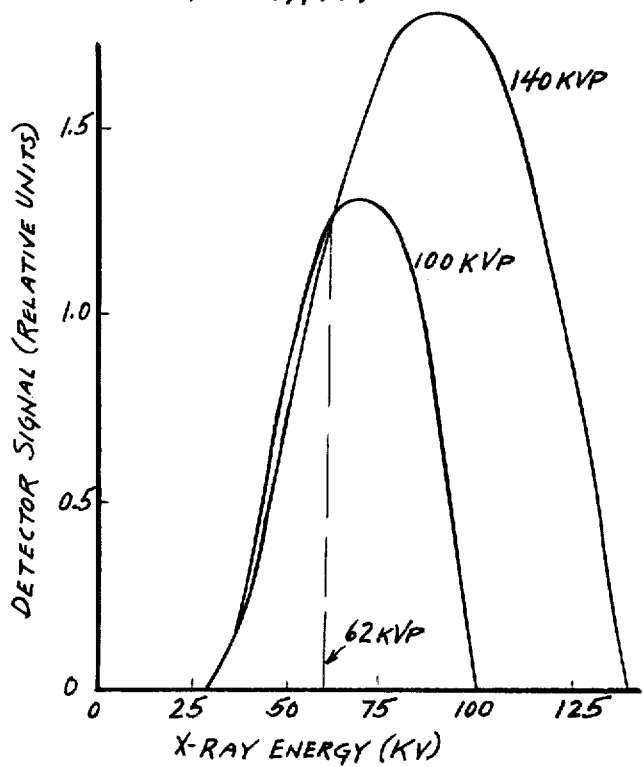
FIG. 4 is a graph showing the detector signals as functions of X-ray energy, as obtained for conventional scans at 100 and 140 kVp.

The plotted curves of FIGS. 3, 4 and 5 illustrate that the split-detector system has better energy discrimination at low energies than the 100–140 kVp method.

The following experiments were performed to test the feasibility of the split-detector method. The crystals were installed and power supply connections were made. The photomultiplier voltage needed depends on both the thickness of the $CaF_2$ crystal and the X-ray tube voltage. For the 8 mm crystal at 120 kVp, a voltage for −700 V on the NaI detector and −800 V on the $CaF_2$ produced satisfactory signals. With the 4 mm $CaF_2$ at 140 kVp, −730 V (NaI) and −930 V ($CaF_2$) were used (these voltages compare with −700 V for the conventional EMI crystals). The higher voltage on the $CaF_2$ photomultiplier was required because CaF has a lower light output, and also the optical transmission is poorer through the long thin crystal.

The energy discrimination of the split-detector was compared with that of conventional scans at 100 kVp and 140 kVp. A 1% KI solution was prepared and placed in a sample bottle in a phantom holder. A split-detector scan was obtained, using the 4 mm CaF2 crystal and 140 kVp on the X-ray tube. The phantom was also scanned with conventional EMI detectors at 100 kVp and 140 kVp. The Hounsfield numbers of the solution were as follows:

| Split-detector | | Dual-kVp | |
|---|---|---|---|
| CaF2: | 296 H | 100 kVp: | 282 H |
| NaI: | 154 H | 140 kVp: | 178 H |
| Difference: | 142 H | Difference: | 104 H |

For this detector configuration the split-detector provided better energy discrimination, as indicated by the difference between the high-energy and low-energy readings. In addition, there is a noise advantage since a 100 kVp scan has more noise per unit dose than a 140 kVp scan.

Finally, two weak solutions were prepared, with attenuation coefficients close to water: 2.5% CaCl2 and 0.2% KI. It was desired to test the ability of the split-detector to distinguish chemicals when the attenuation level is close to that of normal tissue. The solutions were chosen to have nearly the same attenuation coefficient in a normal scan. A conventional scan was obtained at 140 kVp, and a split-detector scan was obtained using the 8 mm CaF2 crystal at 140 kVp . The Hounsfield numbers for the solutions were:

| Solution | Normal Scan | Split-detector | | |
|---|---|---|---|---|
| | | CaF2 | NaI | Difference |
| 2.5% CaCl2: | 44 H | 56 H | 31 H | 25 H |
| 0.2% KI: | 43 H | 55 H | 27 H | 28 H |

The experimental error is less than 1 H, since averages were taken over a large number of pixels.

The interpretation is as follows: for both solutions it is primarily the photoelectric effect that raises the Hounsfield number from 0 to 44 H and 43 H. This is why the CaF2 detector produces about twice the value of the NaI detector, since the CaF2 detects primarily low-energy photons which are more highly attenuated by photoelectric absorption. However, the difference is greater for KI than for CaCl2, because iodine has a high atomic number; hence, there is a greater difference between the split-detector readings for KI. Thus, the method can make the chemical distinction between KI and CaCl2, even at low concentration levels.

In view of the foregoing it will be apparent that the above-described split-detector technique offers a practical method for obtaining chemical information from dual-energy scans. The system is easily adaptable to a conventional two-slice scanner, and produces two simultaneous images which provide energy-dependent information that can be used for making sensitive chemical differentiation. The split-detector configuration can be suitably optimized and used with a suitable data processing method, for example, as described in Brooks (B), so that separate Compton and photoelectric images may be obtained. Also, the herein-described system can be used to implement the beam hardening correction of raw projection data proposed by Alvarez and Macovski (6).

While a specific embodiment of an improved dual-energy system for use in computer assisted tomography has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

For example, the method can be applied to a multiple or fan-beam scanner, wherein each detector element consists of a split detector as previously described. The method can be applied to a multiple or fan-beam scanner containing split detectors wherein the detector elements can be connected in different fashions to offer either dual-energy low-resolution images or single-energy high-resolution images.

What is claimed is:

1. In a computerized tomography apparatus of the type including a detector system and having means to generate an X-ray scanning beam and to pass said beam through material to be examined, the improvement wherein the detector system comprises two overlapping energy-sensing portions which are located in the exit path of said scanning beam, one of said portions being a front energy sensing portion including a first input crystal of calcium fluoride responsive primarily to low-energy photons and allowing most high-energy photons to pass therethrough, the other sensing portion including a second input crystal of sodium iodide responsive to said high energy photons, said portions generating respective signals derived from two different but overlapping energy ranges of the X-ray beam which is to be processed to provide energy dependent attenuation data resulting from the passage of said scanning beam through the material under study.

2. The improved tomography apparatus of claim 1, and wherein said front energy-sensing portion is relatively thin as compared with said other sensing portion.

3. The improved tomography apparatus of claim 1, and wherein said front energy-sensing portion comprises a relatively thin plate-like element integrally formed on said first input crystal.

4. The improved tomography apparatus of claim 3, and wherein said other sensing portion is relatively thick as compared with said front energy-sensing portion.

5. The improved tomography apparatus of claim 4, and wherein said other sensing portion is recessed to receive said front sensing portion.

6. A improved tomography apparatus of claim 1, wherein said second imput crystal is provided with a recess in which said first input crystal is positioned.

7. A improved tomography apparatus of claim 1, wherein said portions have substantially equal outputs at an X-ray beam energy boundary of approximately 62 kVp.

8. In a method of computer assisted tomography including employing a polyenergetic X-ray scanning beam directed through material under examination and obtaining energy-dependent attenuation data, the improvement wherein the obtaining step comprises simultaneously intercepting selected different energy ranges of photons in the exit X-ray beam leaving the material by first passing the X-ray beam through crystalline calcium fluoride to capture low-energy photons and then passing the remainder of said exit beam into crystalline sodium iodide to capture the remaining high-energy photons, and converting the selected different-energy photons into respective two output electrical signals which are in accordance with the attenuation characteristics of the material at the selected different photon energy ranges.

9. The method of claim 8, and wherein the intercepting and converting steps comprise causing the selected photons to generate light, and photoelectrically measuring the intensity of the generated light.

10. The method of claim 8, and wherein one selected range of photons is of relatively low energy and another selected range is of the remaining photons of relatively high energy.

11. The method of claim 10, and wherein the converted output electrical signals are equal at an exit X-ray beam energy boundary of approximately 62 kVp.

12. In a method of computer assisted tomography including employing a polyenergetic X-ray scanning beam directed through material under examination and obtaining energy-dependent attenuation data, the improvement wherein the obtaining step comprises intercepting the low-energy photons in the exit beam and converting said low-energy photons into a "low-energy" electrical signal, and simultaneously intercepting the high-energy photons in the exit beam and converting said high-energy photons into a "high energy" electrical signal, wherein the intercepting of the low and high energy photons takes place by passing the exit X-ray scanning beam sequentially through a first crystal responding to low-energy photons and then into a second crystal responding to high-energy photons, and wherein the intercepting of the low and high energy photons comprises first passing the exit X-ray scanning beam through crystalline calcium fluoride to capture the low-energy photons and then passing the remainder of said exit beam into crystalline sodium iodide to capture the remaining high-energy photons to generate respective signals derived from two different but overlapping energy ranges of the X-ray beam which is to be processed to provide the energy dependent attenuation data resulting from the passage of the X-ray scanning beam through the material under study.

13. The method of claim 12, and wherein the first intercepting and converting steps comprise generating optical scintillations in a low energy-sensitive crystal constituted of said crystalline calcium fluoride and photoelectrically detecting the scintillations, and wherein the second intercepting and converting steps comprise then generating optical scintillations in a high energy-sensitive crystal constituted of said crystalline sodium iodide and photoelectrically detecting the last-named scintillations.

* * * * *